United States Patent [19]

Chance

[11] 4,405,806

[45] Sep. 20, 1983

[54] BROMINE-CONTAINING 2,4-DIAMINOTRIAZINES

[75] Inventor: Leon H. Chance, New Orleans, La.

[73] Assignee: The United States of America as represented by the Secretary of Agriculture, Washington, D.C.

[21] Appl. No.: 370,009

[22] Filed: Apr. 20, 1982

Related U.S. Application Data

[62] Division of Ser. No. 276,768, Jun. 24, 1981, Pat. No. 4,352,930.

[51] Int. Cl.$^3$ .......................................... C07C 101/44
[52] U.S. Cl. ..................................................... 560/43
[58] Field of Search .......................................... 560/43

[56] References Cited

U.S. PATENT DOCUMENTS 3,413,340  11/1968  Wallingford ........................... 560/43
3,766,244  10/1973  Giacobbe et al. ...................... 560/43

Primary Examiner—Bernard Helfin

Attorney, Agent, or Firm—M. Howard Silverstein; David G. McConnell; Raymond C. VonBodungen

[57] ABSTRACT

The following new compounds, useful in flame retardant compositions for cotton, are disclosed in the invention:

2,4-diamino-6-carbamoylmethyl-1,3,5-triazine (Ib),
2,4-diamino-6-(dibromocyanomethyl)-1,3,5-triazine (IIa),
2,4-diamino-6-(dibromocarbamoylmethyl)-1,3,5-triazine (IIb),
2,4-diamino-6-(3,5-dibromo-4'-aminophenyl)-1,3,5-triazine (IIc),
ethyl N-(2,4,6-tribromophenyl)glycinate (IV),
N-(2,4,6-tribromophenyl)glycinamide (V),
2,4-bis[di(hydroxymethyl)amino]-6-(3,5-dibromo-4'-aminophenyl)-1,3,5-triazine (III),
2,4-diamino-6-(2',4',6'-tribromoanilinomethyl)-1,3,5-triazine (Id), and
2,4-bis[di(hydroxymethyl)amino]-6-(2',4',6'-tribromoanilinomethyl)-1,3,5-triazine (VI).

1 Claim, No Drawings

BROMINE-CONTAINING 2,4-DIAMINOTRIAZINES

This is a division, of application Ser. No. 276,768 filed June 24, 1981 and now U.S. Pat. No. 4,352,930.

BACKGROUND OF THE INVENTION

1. Field of the Invention

This invention relates to new organic compounds and processes for the synthesis of the compounds. More specifically, the invention relates to bromine-containing 2,4-diaminotriazines and to esters used as intermediates in the synthesis of said compounds. The bromine-containing 2,4-diaminotriazines can be used to reduce the flammability of cotton.

2. Description of the Prior Art

Chance and Timpa reported an example of a brominated diaminotriazine (Chance, L. H.; Timpa, J. D., J. Chem. Eng. Data 1977, 22, 116, and Chance L. H. and Timpa, J. D., U.S. Pat. No. 4,055,720, 1977). They prepared 2,4-diamino-6-(3,3,3-tribromo-1-propyl)-1,3,5-triazine by the reaction of ethyl γ-tribromobutyrate with biguanide. Ostrogovich reported 2,4-diamino-6-tribromomethyl-1,3,5-triazine prepared by the direct bromination of 2,4-diamino-6-methyl-1,3,5-triazine. (Ostrogovich, A. Chem. Zentrabl. 1905, 2, 1358). Chance reported the preparation of the compounds of the present invention. (Chance, L. H., J. Chem. Eng. Data 1980, 25(4), 402).

SUMMARY OF THE INVENTION

The main object of the invention is to synthesize new bromine-containing 2,4-diaminotriazines.

A second object of the invention is to synthesize the appropriate esters to be used as intermediates in the synthesis of the said bromine-containing 2,4-diaminotriazines.

A third object of the invention is to demonstrate that said bromine-containing 2,4-diaminotriazines can be used to reduce the flammability of cotton.

DESCRIPTION OF THE PREFERRED EMBODIMENTS

In this invention compounds Ia-d were prepared by the reaction of biguanide with the appropriate ester $YCO_2Et$, as shown by the following equation:

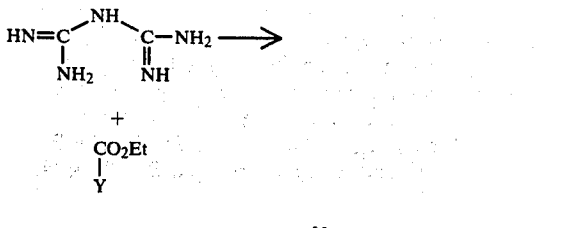

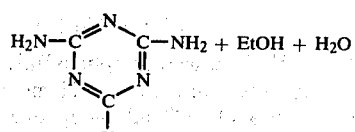

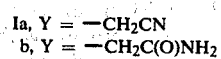

Ia, Y = —CH$_2$CN
b, Y = —CH$_2$C(O)NH$_2$

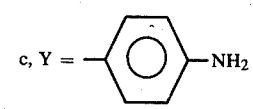

c, Y =

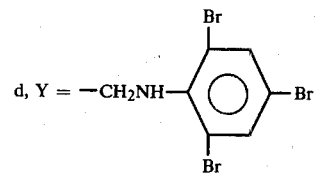

d, Y = —CH$_2$NH—

The ester required for Id, ethyl N-(2,4,6-tribromophenyl)glycinate (IV), was prepared by the reaction of ethyl N-phenylglycinate with bromine in a mixture of water and acetic acid. IV reacted with ammonia is ethanol solution to form N-(2,4,6-tribromophenyl)glycinamide (V).

Compounds Ia-c were then allowed to react with bromine in aqueous media to form diaminotriaizines IIa-c.

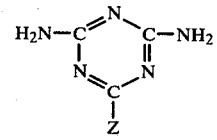

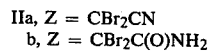

IIa, Z = CBr$_2$CN
b, Z = CBr$_2$C(O)NH$_2$

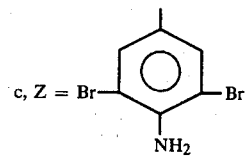

c, Z =

Crystalline methylol derivatives of IIc and Id, viz. III and IV, respectively, were prepared by reaction with aqueous formaldehyde.

Compounds I b,d, IIa-c, III, Iv, V and VI are new compositions of matter.

Biguanide was prepared fresh by refluxing anhydrous biguanide sulfate in a methanol solution of freshly prepared sodium methylate by the method of Slotta et al. (Slotta, K. H., Tschesche, R., Ber. Dtsch. Chem. Ges. 1929, B62, 1390-1398). The biguanide was used in solution as prepared for all of the reactions. Because sodium sulfate formed in the preparation of biguanide did not interfere with subsequent reactions, it was not necessary to separate it from the biguanide. Ethyl malonamate used in the preparation of Ib (see Example 1 below) was prepared as follows by methods of Galat and Marguery (Galat, A., J. Am. Chem. Soc. 1948, 70, 2596 and Marguery, M. F., Bull. Soc. Chem. France 1905, 33, 541; J. Recherces Centr. Natl. Recherche Sci., Labs. Bellevue (Paris) 1959, 47, 147), through Chem. Abstr. 1962, 56, 4744 g.): Diethyl malonate was converted to the monopotassium salt of the half-ester. The latter was converted to ethyl malonyl chloride, which in turn was reacted with anhydrous ammonia in ice-cold ether to form ethyl malonamate.

Compounds IIa, IIb, III,V, and VI were applied to cotton flannelette fabric by padding and drying procedures conventionally used in the finishing of cotton textiles. The said compounds were applied to the fabric from dimethylformamide solution. The fabrics had reduced flammability as indicated by oxygen index. The oxygen index values for cotton fabric treated with compounds IIA, IIb, III, V, and VI were 33.8, 31.0, 22.1, 23.0, and 22.1, respectively. An untreated control fabric had an oxygen index of 18.5, indicating that all treated fabrics were less flammable than the control. All of the treated fabric samples contained approximately 8% bromine. The oxygen index analyses were carried out on a Stanton Redcroft instrument using the procedure set forth in ASTM D 2863-70.

The following examples illustrate procedures that have been successfully used in carrying out the invention.

EXAMPLE 1

2,4-Diamino-6-carbamoylmethyl-1,3,5-triazine (Ib). Ethyl malonamate (34.7 g, 0.26 mole) and methanol (100 ml) were placed in a flash equipped with a dropping funnel, a stirrer, and a soda lime trap (to exclude $CO_2$). The flask was cooled to about 15° C. in an ice-water bath. Freshly prepared biguanide (26.3 g, 0.26 mole, in 250 ml methanol) was added, with stirring, over 35 ml at 15°-20° C. A white precipitate began to form within 8-9 min. The mixture was allowed to stir overnight at room temperature. It was then cooled to 15° C., and the white precipitate was filtered, washed with cold water to remove sodium sulfate, and finally washed with cold methanol. A crude yield of 32.7 g (76%) was obtained. A pure sample recrystallized from water had a mp of 295°-96° C. (dec.) when placed in a preheated bath at 295° C. Anal. calcd. for $C_5H_8N_6O$: C, 36.59; H, 4.91; N, 48.76. Found: C, 36.73; H, 5.08; N, 48.51.

EXAMPLE 2

2,4-Diamino-6-(dibromocyanomethyl)-1,3,5-triazine (IIa). Ia(15.0 g, 0.1 mole) and 250 ml water were placed in a flask equipped with a reflux condenser, stirrer, and dropping funnel. Bromine (32.0 g, 0.2 mole) was added dropwise to the resulting slurry with vigorous stirring over 20 min. The mixture was stirred at room temperature for 1.5 h and then placed in a refrigerator overnight. The light-gray precipitate was filtered and washed with cold water. A crude yield of 26 g (83%) was obtained. A pure sample was obtained by dissolving 3 g of IIa in 5 ml of dimethylformaldehyde, filtering, and pouring the solution into 75 ml water. The resulting precipitate was washed with cold water and finally with cold methanol. The grayish crystals had a mp of 238°-40° C. (dec.) when placed in a bath preheated to 238° C. Anal. calcd. for $C_5H_4Br_2N_6$: C, 19.50; H, 1.31; Br, 51.90; N, 27.29. Found: C, 19.70; H, 1.24; Br, 51.69; N, 27.37.

EXAMPLE 3

2,4-Diamino-6-(dibromocarbamoylmethyl)-1,3,5-triazine (IIb). Ib (16.4 g, 0.1 mole) and 250 ml water were placed in a flask equipped with a reflux condenser, stirrer, and dropping funnel. Bromine (32.0 g, 0.2 mole) was added dropwise over 2.5 h. The temperature reached a maximum of only 30° C. during the addition. The reaction mixture was cooled in ice water and the crystals were filtered. They were washed with ice water, and then with cold methanol. The cream-colored crystals weighed 11.9 g. A second crop of crystals (13.2 g) was obtained by adjusting the pH of the filtrate to 7.1 by adding 29% ammonium hydroxide (25.7 g, 0.44 mole). The total yield of crude IIb was 25.1 g, (78%). A purer sample of white crystals was obtained by recrystallization from water. The mp was 219°-20° C. (dec.) when a sample was placed in a bath preheated to about 215° C. Anal. calcd. for $C_5H_6Br_2N_6O$: C, 18.65; H, 1.88; Br, 49.03; N, 24.86. Found: C, 18.83; H, 1.99; Br, 48.24; N, 25.72.

EXAMPLE 4

2,4-Diamino-6-(3,5-dibromo-4'-aminophenyl)-1,3,5-triazine (IIc). Ic (10.0 g, 0.05 mole), 150 ml conc. hydrochloric acid, and 450 ml water were placed in a flask equipped with a reflux condenser, stirrer, and dropping funnel. Ic was dissolved by heating the stirred mixture to 65° C. on a water bath. Bromine (16.5 g, 0.1 mole) was added dropwise over 10 min. A precipitate began to form as soon as the bromine addition was begun. Heating and stirring at 65° C. was continued for 3 h. The mixture was cooled to room temperature and allowed to stand overnight. After the mixture was cooled in ice water the crystals were filtered, slurried with cold acetone, and filtered again. The pale-yellow crystals weighed 17.3 g. They were placed in distilled water (450 ml) and adjusted with good stirring to pH 7.8 with conc. ammonium hydroxide to neutralize any amine hydrochloride salts that may have been present. The resulting thick slurry was filtered, and the precipitate was washed with water and pressed as dry as possible on the filter. After being air dried the cream-colored crystals weighed 15.5 g, a crude yield of 88% of IIc. A pure sample was obtained by dissolving 1.5 g in DMF (5.0 g) at 125° C. While the solution was kept hot, water (1.2 g) was added dropwise with stirring until a slight turbidity appeared. The white crystals that separated upon cooling were filtered and washed with a DMF/$H_2O$ mixture. They were finally washed with ethanol and dried at 110° C. The mp was 289° C. (dec.) when placed in a bath preheated to 289° C. Anal. calcd. for $C_9H_8Br_2N_6$: C, 30.03; H, 2.24; Br, 44.39; N, 23.34. Found: C, 29.89; H, 2.25; Br, 44.23; N, 23.56.

EXAMPLE 5

2,4-Bis[di(hydroxymethyl)amino]-6-(3,5-dibromo-4'-aminophenyl)-1,3,5-triazine (III). IIc (8.0 g, 0.22 mole) and 37% aqueous formaldehyde (110 g) were placed in a flask and adjusted to pH 7.8 by the addition of 5% NaOH (0.7 g). The mixture was refluxed for 20 min. The clear solution was cooled to room temperature and allowed to stand for 3-4 h. The white precipitate obtained was filtered and washed with 25 ml of 37% formaldehyde. It was then slurried with 100 ml of water, filtered, and washed again with 50 ml of water. After being thoroughly air dried, it weighed 8.4 g (89% yield). The crystalline compound had a mp of 165°-66° C. (dec.) when placed in a bath preheated to 165° C. Anal. calcd. for $C_{13}H_{16}Br_2N_6O_4$: C, 32.52; H, 3.36; Br, 33.29; N, 17.50. Found: C, 31.93; H, 3.41; Br, 32.74; N, 17.46.

EXAMPLE 6

Ethyl N-(2,4,6-tribromophenyl)glycinate (IV). Ethyl N-phenylglycinate (20.0 g, 0.11 mole), water (500 ml), and acetic acid (100 ml) were placed in a 1-L flask equipped with a reflux condenser, a stirrer, and a dropping funnel. Bromine (52.7 g, 0.33 mole) dissolved in acetic acid (100 ml) was added dropwise with good stirring over 2 h. At first, a viscous material formed and adhered to the walls of the flask. Eventually it solidified. The solid was scraped off the walls as the bromine addition progressed. The mixture was stirred for an additional 2 h. At this point the bromine color had disappeared. The mixture was cooled in ice water. The crude pale-gray crystals were filtered and recrystallized from 500 ml of boiling methanol. The yield was 31.4 g (68.5%) of white needles, mp 81°–82° C. Anal. calcd. for $C_{10}H_{10}Br_3NO_2$: C, 28.88; H, 2.42; Br, 57.64; N, 3.37. Found: C, 28.80; H, 2.46; Br, 57.42; N, 3.32.

EXAMPLE 7

N-(2,4,6-tribromophenyl) glycinamide (V). IV (7.5 g, 0.018 mole) and absolute ethanol (300 ml) were placed in a flask and warmed slightly to dissolve all of the crystals. Then the solution was saturated with anhydrous ammonia while the flask was cooled in ice water. White needles separated after the clear solution stood at room temperature for 3 days. The mixture was cooled in ice water, and the crystals were filtered and washed with a small amount of cold ethanol. A second crop of crystals, 1.1 g, was obtained by evaporating the filtrate to a volume of 35 ml and cooling in ice water. The total yield was 6.1 g (89%), mp 185°–185.5° C. Anal. calcd. for $C_8H_7Br_3N_2O$: C, 24.84; H, 1.82; Br, 61.96; N, 7.24. Found: C, 24.83; H, 1.87; Br, 61.82; N, 7.26.

EXAMPLE 8

2,4-Diamino-6-(2',4',6'-tribromoanilinomethyl)-1,3,5-triazine (Id). Freshly prepared biguanide (6.1 g, 0.06 mole) in methanol (700 ml) was placed in a flask equipped with a stirrer and a soda lime trap to exclude $CO_2$. IV (25.0 g, 0.06 mole) was added all at once through a powder funnel. After the solution was stirred for 10 min at room temperature, a white precipitate began to form. After being stirred for 7.5 h, the mixture was allowed to stand overnight. The crystals were filtered and washed with fresh methanol. They were then slurried with water (250 ml), filtered again, and washed with methanol. A crude yield of 21.9 g (81%) was obtained. It was recrystallized by dissolving 21.8 g in 80 ml of hot DMF (125° C.) and then adding 9 ml of water dropwise. When the solution cooled, white crystals separated. A second crop of crystals was obtained from the filtrate. The total recovery was 15.5 g, a yield of 57% based on the theoretical yield of 27.2 g. An analytical sample with mp of 250°–51° C. was obtained by recrystallizing again from hot DMF and finally washing with cold methanol. Anal. calcd. for $C_{10}H_9Br_3N_6$: C, 26.52; H, 2.00; Br, 52.93; N, 18.55. Found: C, 26.52; H, 2.02; Br, 52.71; N, 18.59.

EXAMPLE 9

2,4-Bis[di(hydroxymethyl)amino]-6-(2',4',6'-tribromoanilinomethyl)-1,3,5-triazine (VI). Id (25.0 g, 0.055 mole) and 37% aqueous formaldehyde (250 ml) were placed in a 500-ml flask and adjusted to pH 9.2 by the addition of 10 drops of 25% NaOH. It was refluxed for 10 min with stirring. During the reflux period, 4 drops more of 25% NaOH were added. After the solution was cooled to room temperature, the pH was readjusted to 9.1 by adding 4 drops more of 25% NaOH. A white precipitate formed as the mixture cooled. After several hours the mixture was cooled in ice water and diluted with ice water to a volume of about 600 ml to complete precipitation. It was filtered, the precipitate was slurried with cold water, filtered again, and washed on the filter with more cold water. After being thoroughly air dried, the white crystals weighed 30.3 g, a 96% yield, mp 137°–8° C. (dec). Anal. calcd. for $C_{14}H_{17}Br_3N_6O_4$: C, 29.34; H, 2.99; Br, 41.83; N, 14.67; Found: C, 29.01; H, 3.31; Br, 40.49; N, 14.12.

I claim:
1. Ethyl N-(2,4,6-tribromophenyl)glycinate.

* * * * *